(12) United States Patent
Hölker (10) Patent No.: US 6,797,508 B1
(45) Date of Patent: Sep. 28, 2004

(54) BIOREACTOR FOR FERMENTING SOLIDS

(75) Inventor: Udo Hölker, Königswinter-Rauschendorf (DE)

(73) Assignee: Hofer Bioreact GmbH, Bonn (DE)

( * ) Notice: Subject to any disclaimer, the term of this patent is extended or adjusted under 35 U.S.C. 154(b) by 2 days.

(21) Appl. No.: 10/070,966

(22) PCT Filed: Sep. 13, 2000

(86) PCT No.: PCT/EP00/08929

§ 371 (c)(1), (2), (4) Date: Jul. 31, 2002

(87) PCT Pub. No.: WO01/19954

PCT Pub. Date: Mar. 22, 2001

(30) Foreign Application Priority Data

Sep. 13, 1999 (DE) .......................................... 199 43 853

(51) Int. Cl.[7] .......................... C12N 1/14; C12P 19/60; C10G 32/00; C12M 1/38; A62C 35/00
(52) U.S. Cl. ...................... 435/252.1; 435/75; 435/243; 435/281; 435/286.7; 169/5; 169/45; 169/68
(58) Field of Search ................................ 169/5, 45, 68; 435/75, 243, 252.1, 281, 286.7

(56) References Cited

U.S. PATENT DOCUMENTS 5,153,137 A * 10/1992 Laurenson, Jr. .......... 435/290.4
5,670,345 A *  9/1997 Srivastava et al. ............ 435/75

FOREIGN PATENT DOCUMENTS

EP  489705 A3 *  2/1993  .............. B01J/4/00
EP  509980 B1 *  1/1995  ............. B09B/1/00

* cited by examiner

Primary Examiner—Leon Blaine Lankford, Jr.
Assistant Examiner—Kailash C. Srivastava
(74) Attorney, Agent, or Firm—Norris McLaughlin & Marcus PA (57) ABSTRACT

The invention relates to bioreactor for fermenting solid substrates, comprising a fermentation vessel (2), a device for feeding bioreactive substances and a nozzle arrangement in the fermentation vessel (2). The invention is characterized in that a nozzle arrangement (10, 20) consisting of a plurality of pipes (14, 24) which project into the reaction chamber (49) of the fermentation vessel (2) in parallel and which are provided with nozzles (16, 28) is situated in the fermentation vessel (2). The invention also relates to a method for aerobically fermenting solids. A reaction medium containing these solids is mixed using a compressed gas (48) which is guided into the reaction mixture from above.

28 Claims, 7 Drawing Sheets

BIOREACTOR FOR FERMENTING SOLIDS

This application is a 371 of PCT/EP00/08929 filed on Sep. 13, 2000.

The present invention relates to a bioreactor for fermenting solids, and a corresponding fermentation method.

The conversion of solid, water-insoluble or particular substances in fermenters involves a wide variety of problems, primarily relating to aeration, mixing and the addition of nutrient media. In addition, if the substrate to be converted is to be synergistically attacked by a number of different microorganisms, it Is required to selectively supply the reaction space with nutrients and oxygen. In large-volume reactors, such fermentations currently cannot be realized due to the complicated mixing and the resulting defective aeration and deficient supply of substrates.

In commercially available reactor systems, the mixing is effected by mechanical agitating systems. In addition, U.S. Pat. No. 4,846,964 describes a fluidized-bed bioreactor system for converting coal to microbiologically liquefied coal products in which an upflowing aqueous stream keeps the coal particles fluidized. The above mixing methods have a drawback in that sufficient mixing and thus a high substrate turnover is no longer possible in the fermentation of higher substrate concentrations or substrates which tend to agglomerate.

Now, it has been the object of the present invention to provide a bioreactor and a fermentation method which overcome the drawbacks of the prior art and, in particular, ensure a sufficient mixing of the substrate to be fermented.

Surprisingly, it has now been found that a sufficient mixing of the reaction medium, which contains solid or water-insoluble fermentation substrates, can be achieved in a bioreactor by purposefully introducing a compressed gas continuously or in compressed gas pulses.

The above object is achieved by a bioreactor having the features as described below, and a method for aerobic fermentation having the features as described below.

The bioreactor serves for the fermentation of water-insoluble or particular substrates, such as wood (which can be degraded only by particular microorganisms due to its lignin content), coals (with the goal of using the liquid fermentation products as starting materials for the chemical industry or for thermal utilization), for the remediation of soils loaded with xenobiotics, for the rapid fermentation of organic waste products, for biological waste water purification, and for the pretreatment of basic materials of the chemical industry.

The proposed bioreactor for the first time permits the optimum aeration and mixing of solid, water-insoluble and particular substances, which is necessary for microorganisms, by using at least one specific nozzle arrangement which is introduced into the substrate to be fermented and pneumatically supplied with compressed gas. Both the supply of oxygen to the microorganisms and the supply thereto of nutrient media, cosubstrates, vitamins, minerals, buffers or antibiotics are effected by a single pneumatic pressure system. In a slightly modified form, the bioreactor can be used In any size from a five-liter laboratory scale to an industrial, multi-hectoliter scale. With simple modifications, the proposed bioreactor can also be used as a conventional liquid/solid phase, solid phase, falling film, fed batch or air-lift reactor.

According to the invention, a first, vertically extending nozzle arrangement can be extended into and retracted from the reaction space of the fermentation vessel. Thus, the nozzle arrangement can be shifted in a vertical direction to enable movement of the nozzle arrangement while pressurized with compressed gas, for a better mixing and aeration. However, if the fermentation process is to proceed under sterile conditions, it is imperative that the reaction space be kept closed. The nozzle arrangement consists of pipes which vertically protrude into the fermentation vessel and are provided with nozzles on their lower ends. In this way, the compressed gas or the liquid bioactive substrate can be introduced near the bottom of the fermentation vessel. The nozzle arrangement is also suitable for penetrating granular solids present in the fermentation broth. The vertical pipes can have different lengths and can be exchanged. Further, the nozzle arrangement, when retracted from the fermentation vessel, can be cleaned in a simple way.

In addition, a second horizontal nozzle arrangement can be provided which consists of interconnected pipes horizontally extending in parallel through the reaction space. The pipes have nozzles distributed on their coat surface.

The horizontal nozzle arrangement can be used for mixing additionally to the vertical nozzle arrangement.

If the horizontal nozzle arrangement is to rotate for a better mixing of the fermentation substrate, the vertical arrangement of nozzles must be moved upwards, or the vertical pipes must be selected so as not to hinder the rotating of the horizontal nozzle arrangement, i.e., the "normal" pipes must be replaced by shorter pipes.

An advantageous further development of the bioreactor according to the invention has a measuring device in which several measuring electrodes, for example, are provided in a measuring chamber for measuring a medium removed from the fermentation vessel. The measuring chamber is connected with the fermentation vessel through a feed line in order to feed medium to be measured from the fermentation vessel into the measuring chamber. To recirculate the medium into the fermentation vessel after measuring, the measuring chamber is further connected with the fermentation vessel through a recirculating line. The special about this arrangement is the fact that a pressure chamber is inserted upstream from the measuring chamber, where a defined pressure can build which corresponds to the displaced volume in the measuring chamber. According to the invention, the recirculation of the measured medium is effected by applying pressure to the measuring chamber so that the medium is pressed back into the fermentation vessel.

In known bioreactors, measurements are usually performed directly within the fermentation vessel. Since solid substances are contained in the fermentation vessel, the measuring electrodes are often damaged. For external measurement, in known bioreactors, the medium to be measured is transported into a measuring chamber by peristaltic pumps. Such pumps are subject to high wear and are not suitable for transporting larger volumes.

Because the medium is transported by pressure according to the invention, such pumps which are subject to wear and thus to intensive maintenance can be dispensed with. Further, it is possible to transport large volumes. Another advantage of transport by pressure is the fact that the sterility is not affected. This means that no foreign matter gets into the fermentation vessel during the pumping process.

The feeding of medium through the feed line into the measuring chamber can be effected by negative pressure. The measuring chamber according to the invention can further be used as an additional recirculation system. Such a recirculation system can perform an additional aeration of the substrates present in the fermentation vessel.

Further advantageous embodiments of the bioreactor can be seen from the further dependent claims.

In the method according to the invention, for the aerobic fermentation of solid substrates, a reaction medium containing such solid substrates is thoroughly mixed by compressed gas introduced from above into the reaction medium. This thorough mixing dramatically increases the fermentation rate. According to the present invention, "to introduce from above into the reaction medium" means that compressed gas is introduced into the reaction medium by means of suitable devices (such as pipes provided with nozzles) which extend into the reaction medium from above. The length of the pipes can be selected to reach below the surface of the reaction medium at any level in the introduced working condition (i.e., with or without introduced compressed gas).

In the following, the invention will be further described by the Figures and Examples, wherein.

Figure 1:
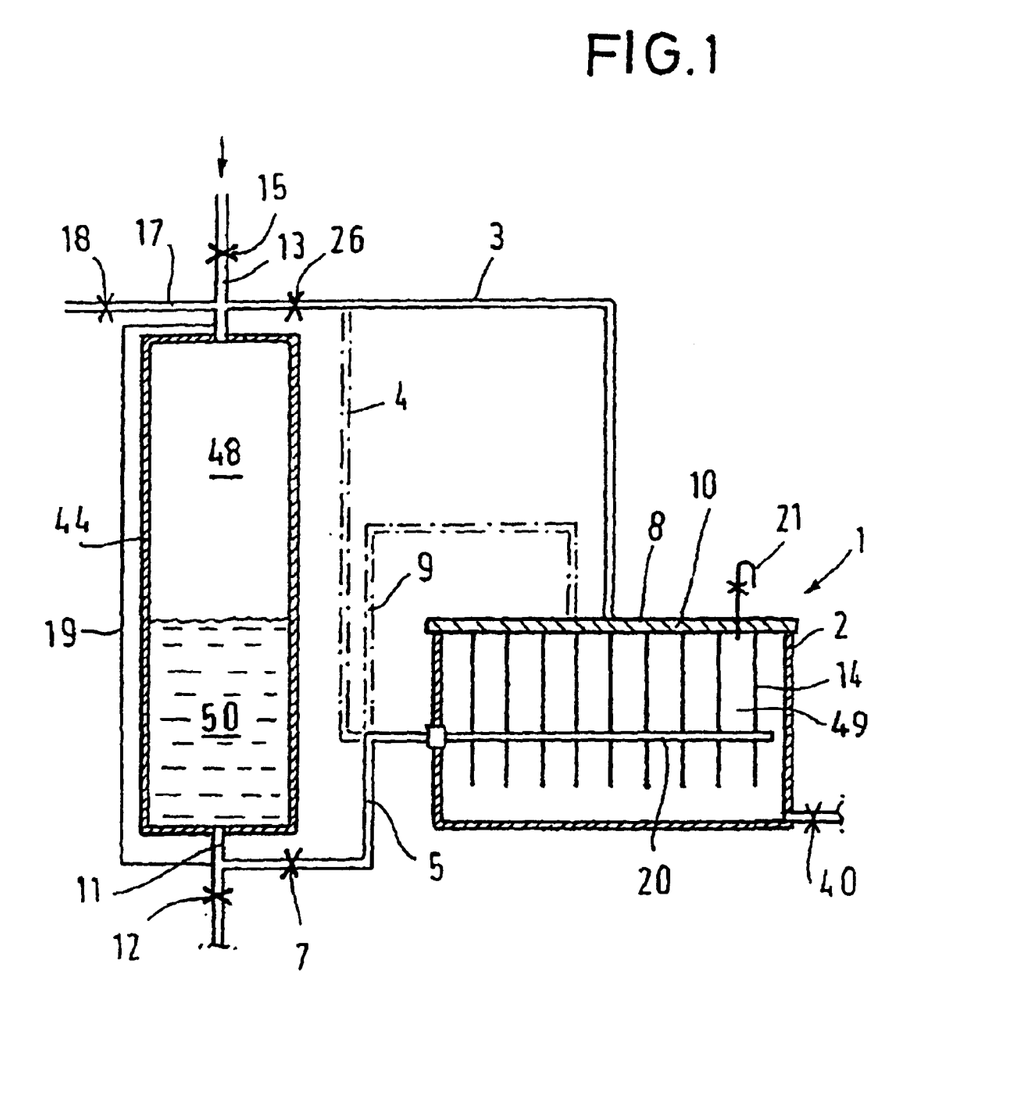
FIG. 1 shows a bioreactor having a pressure vessel for bioreactive substances and for compressed air.

The bioreactor shown In FIG. 1 for the fermentation of solid substrates and for performing one of the fermentation processes described in more detail below has a fermentation vessel 2 which can be hermetically sealed with a pressure lid 8.

Fermentation vessel 2 is provided with at least one nozzle arrangement 10, 20 extending into the reactor space 49 to which compressed air 48 is supplied through a pressure vessel 44, through a compressed gas line 3 for a vertical nozzle arrangement 10 and through a compressed gas line 4 for a horizontal nozzle arrangement 20.

The pressure vessel 44 additionally contains a bioreactive liquid substance 50 which can be supplied through a stop valve 7 and a pressure line 5 to the horizontal nozzle arrangement 20, and/or through a pressure line 9 to the vertical nozzle arrangement 10.

Consequently, the vertical nozzle arrangement 10 and/or the horizontal nozzle arrangement 20 may also be used as a supply means for bioreactive substances as an alternative of pressurizing with compressed gas.

On the bottom of the pressure vessel 44 is provided a discharge line 11 with a stop valve 12. On the top end of the pressure vessel 44 is provided a feed line 13 for supplying bioreactive substances 50 and a stop valve 15.

The compressed gas 48, e.g., compressed air, is supplied through a feed line 17 and a stop valve 18.

Juxtaposed to the pressure vessel 44 is a rising pipe 19.

The fermentation 2 further has a pressure compensating means 21 with a stop valve. On the bottom of the fermentation vessel 2, a draining channel 36 covered by a wire mesh 38 is provided below a conical bottom section 32 (FIG. 2), so that liquid contained in the fermentation vessel 2 is coarse-filtered prior to being discharged into the draining channel. The bottom of the draining channel 36 is inclined from horizontal, a draining valve 40 being provided at the front side 51 of the fermentation vessel at the lowest position of the draining channel 36.

Figure 3:
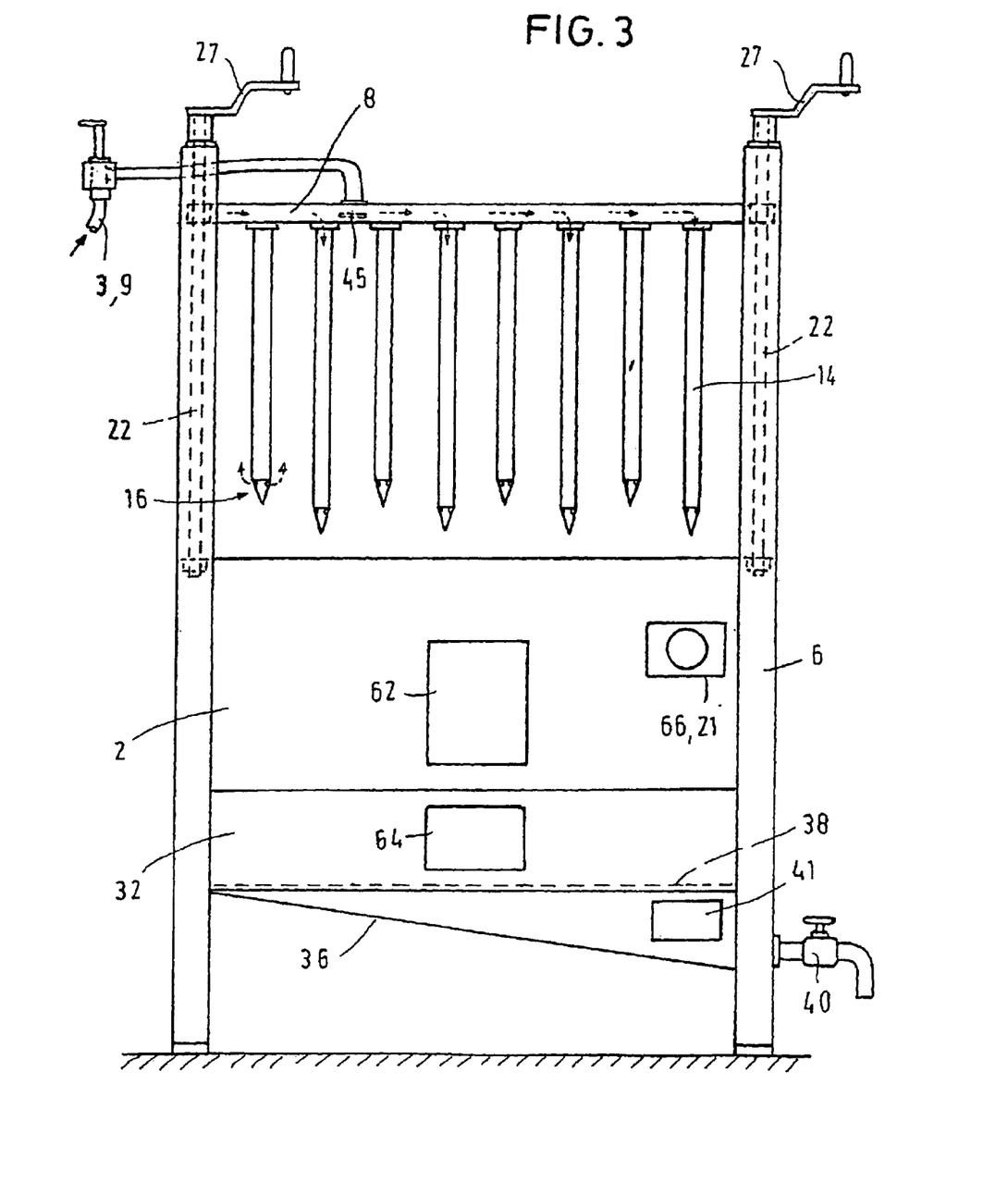
FIG. 3 shows a side view of the bioreactor.

On the front side 51 of the fermentation vessel 2 is provided a removable door 53 to enable cleaning of the interior space and of the wire mesh 38 without having to open the cover plate 8 sealing the reactor space 49. On the draining channel 36 are provided two windows 41 facing each other, which enable determination of the optical density of the fermented substance with an optical sensor (FIG. 3). Additional windows 62, 64 provided on the lateral walls enable visual control of the fermentation conditions, but these are not obligatory.

Instead of or in addition to a subsequently described external measuring chamber 72, on one side of the fermentation vessel 2, there may be provided a sealable means 66 for measuring electrodes (e.g., pH, $O_2$ partial pressure, conductivity, ion specificity etc.) and a pressure compensating means 21 for the controlled exhausting of air or gases formed during fermentation from the fermentation vessel 2.

All components which will come into contact with medium or gases can be independently autoclaved.

The bioreactor according to the invention can further have devices for heat exchange, i.e., heating and cooling. Thus, the fermentation vessel 2 can have a double wall to form a cavity 51a. This cavity is formed between the inner and outer walls of vessel 2. The cavity 51a is connected, for example, with a correspondingly temperature-controlled heat exchange fluid reservoir (e.g., water or oil reservoir) through a connecting pipe 51b and discharge pipe 51c. The water or oil which has a defined temperature due to an external thermostat flows around vessel 2. Due to this device, the bioreactor can be operated with stepless control in a temperature range of from 10 to 90° C., whereby, on the one hand, the optimum temperature for the different microorganisms can be adjusted in the bioreactor, and on the other hand, the whole bioreactor including its contents can be mildly sterilized or tyndallized. Therefore, such a sterilization/tyndallization of a whole bioreactor in an integrated system, which has not been previously described as such, has significant advantages in the application of the system.

Figure 2:
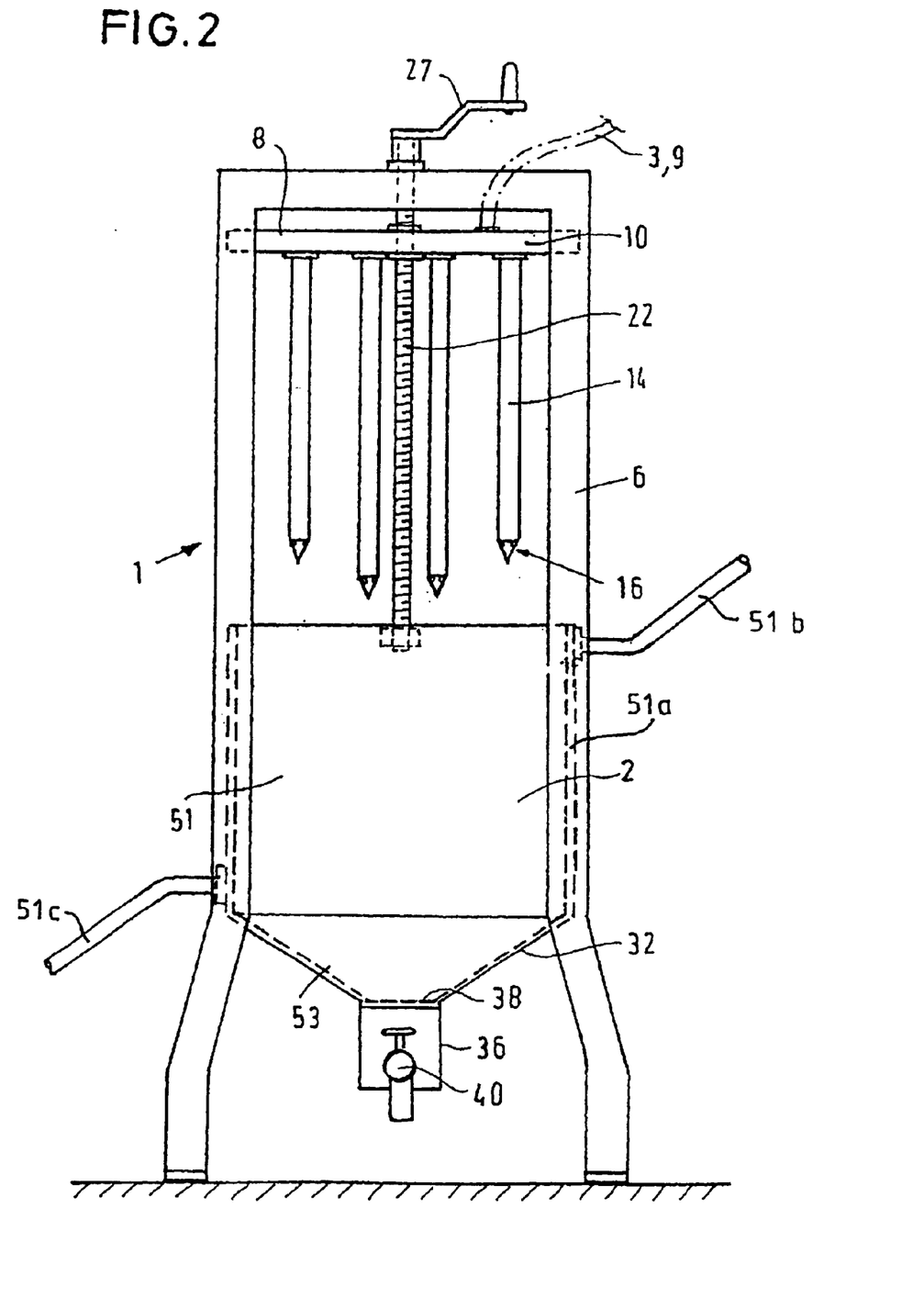
FIG. 2 shows a frontal view of the bioreactor.

As can be seen from FIGS. 2 and 3, the fermentation vessel 2 is held by a frame 6. The frame 6 also accommodates two spindles 22 by means of which the pressure lid 8 of fermentation vessel 2 can be lowered onto the latter or lifted. The pressure lid 8 at the same time forms the vertical nozzle arrangement by effecting the supply of compressed gas or bioreactive substances through the pressure lid 8 to the vertical pipes 14 extending vertically from the pressure lid 8. The vertical pipes 14 can be of different lengths, the tips of the pipes 14 with nozzles 16 being positioned in the bottom portion of the fermentation vessel when the pressure lid 8 is closed, By lowering the pressure lid, the nozzles 16 can also penetrate solid substrates present in the reactor space. In the closed position of the pressure lid, the fermentation vessel 2 can be hermetically sealed.

The spindles 22 are actuated by means of crank handles 27 provided on the top of frame 6.

A hollow pressure plate 8 serves as the pressure lid of bioreactor 1, being one of two possibilities for aerating the bioreactor space in the fermentation vessel 2 or supplying it with media. It can be vertically guided by rails and hermetically seals the fermentation vessel 2 during operation. When the bioreactor 1 is to be charged with the substrate to be converted, the pressure lid 8 can also be lifted hydraulically or pneumatically in addition to the mechanical way described above.

On its top side, pressure lid 8 has a manually or electronically controllable port for supplying compressed air (or defined gases). Optionally, the port may also be used for the supply of liquid defined media, e.g., required cosubstrates, vitamins, minerals, buffers or antibiotics. Within pressure lid 8, the air first impinges on a baffle 45. On the lower side of pressure lid 8, exchangeable pipes 14 with nozzles 16 are screwed into threads. When pressure builds in the pressure lid 8, the air continuously flows through the nozzles 16 provided at the tips of pipes 14 into the reactor space 49 of fermentation vessel 2, aerating it uniformly. In addition to the mild mixing of the reactor space by the continuous flow of air, a thorough mixing of the reactor space can optionally be effected by strong pulses of compressed air applied in defined intervals.

Due to the different lengths of the exchangeable pipes 14 which can be screwed into the pressure lid 8, it is possible to aerate the reactor space 49 in a well-aimed manner. By nozzles 16 extending to the bottom of fermentation vessel 2, a homogeneous aerobic reaction space can be achieved. When shorter nozzles are selected, a defined space having a lower oxygen partial pressure is generated. The bioreactor 1 can be operated either without gassing (in which case the threads of pressure lid 8 can be closed by blind stoppers), or in an obligatory anaerobic mode by supplying defined gases free of $O_2$. In this case, any media to be added should be degassed before being supplied.

Optionally, liquid media may also be added to bioreactor 1 from the pressure or mixing vessel 44, 46 through these nozzles 16. In this case, aeration, if required, may also be effected by the nozzle arrangement 20 extending horizontally through reactor space 49.

Figure 4:
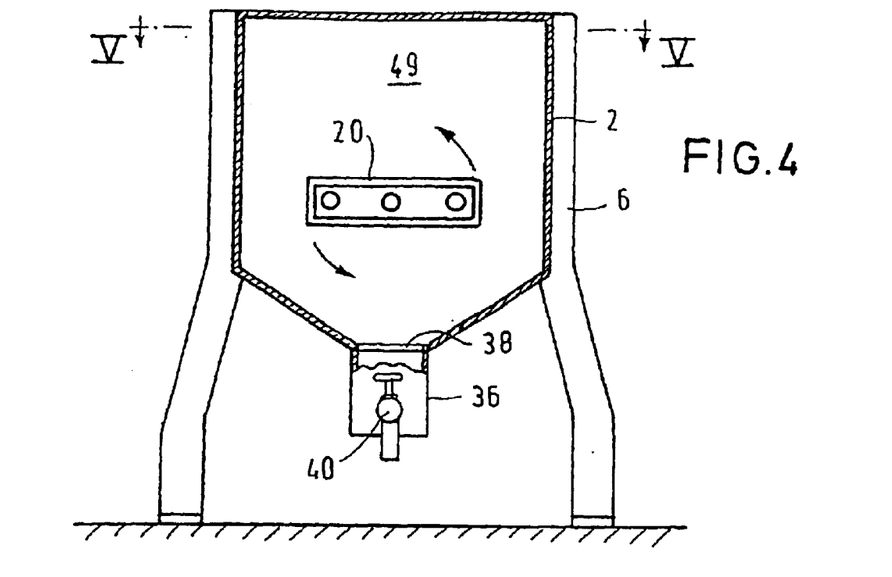
FIG. 4 shows a cross-sectional view through the fermentation vessel of the bioreactor.
Figure 5:
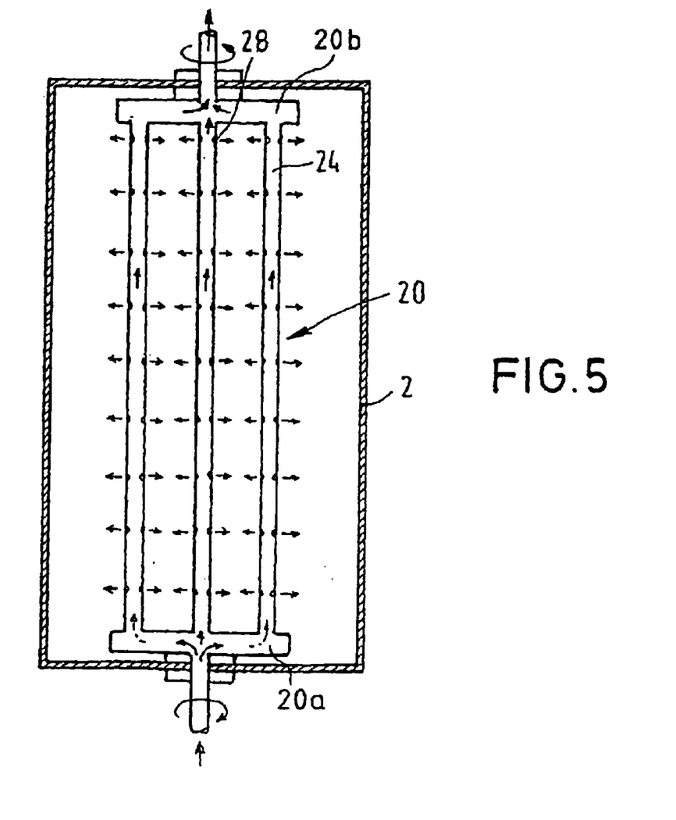
FIG. 5 shows a cross-sectional view along line V—V in FIG. 4.

FIGS. 4 and 5 show the nozzle arrangement 20 provided horizontally within fermentation vessel 2, which can be pressurized with either compressed air 48 or a liquid bioreactive substance 50. As can be seen from FIG. 5, the horizontal nozzle arrangement 20 can be supported on one side in a front wall of fermentation vessel 2 or on both sides in the front walls. Further, the horizontal nozzle arrangement may be designated for support at different levels on the front wall.

As can be seen from FIG. 5, the horizontal nozzle arrangement 20 consists of three pipes 24 each having a plurality of nozzle orifices 28 extend horizontally in parallel through fermentation vessel 2. The three pipes 24 are interconnected through an inlet manifold 20a and an outlet manifold 20b.

As can be seen from FIG. 5, the horizontal nozzle arrangement 20 can be rotated around a horizontal rotation axis to additionally achieve a thorough mixing of the vessel contents. When the horizontal nozzle arrangement 20 is rotated, the length of pipes 14 of the vertical nozzle arrangement 10 is to be selected to preclude collision between pipes 14 and pipes 24. Alternatively, if sterility of the fermentation process is not required, the vertical nozzle arrangement may be retracted vertically upwards to such an extent that a collision between pipes 14 and 24 cannot occur. To maintain sterile conditions, the rotating horizontal nozzle arrangement 20 is preferably provided at the lowest possible position within fermentation vessel 2. In this case, the pipes 14 are preferably shortened to the extent as just not extending into the rotating area. In this case, the outermost pipes 14 which are provided close to the sides of fermentation vessel 2 are longer than the pipes provided further inwardly.

The outlet manifold 20b can have a valve for closing the outlet, or it may also be used as an inlet manifold, in which case the material supplied to the pipes 24 must completely pass through the nozzle orifices 28. The outlet manifold 20b may also be completely omitted. However, this requires a more stable construction of nozzle arrangement 20.

The nozzle arrangement 20 may also be used for heating/cooling by closing the nozzles 28, or by replacing the nozzle arrangement 20 by a corresponding pipe system without nozzles. In this case, the inlet manifold 20a serves for supplying the temperature-controlled heating/cooling fluid, and the outlet manifold 20b serves as a discharge thereof. Such a nozzle arrangement 20 designed as a cooling arrangement may also be rotating. Further, several nozzle/cooling arrangements may be provided, so that a rotating horizontal nozzle arrangement and a rotating horizontal cooling arrangement, for example, can be provided simultaneously in one vessel 2.

Of course, it is possible to pressurize the vertical nozzle arrangement 10 with compressed gas 48 and to pressurize the horizontal nozzle arrangement 20 with the bioreactive substance 50, or vice versa.

The second nozzle arrangement 20 extends horizontally through the reactor space 49. It can be Introduced at different levels and is supported to rotate around its axis, Such a nozzle arrangement is used for supplying the bioreactor with liquid defined media, e.g., water, required cosubstrates, vitamins, minerals, buffers or antibiotics, but may optionally be used for aerating and mixing the bioreactor 1. For the fermentation of liquid or water-soluble substances, the horizontal nozzle arrangement may be rotated by a motor provided on the outer side of bioreactor 1 and thus contribute to a thorough mixing of the bioreactor contents. In this case, shorter vertical pipes 14 are employed, and the horizontal nozzle arrangement 20 is inserted in its lowermost lock.

The mixing of the bioreactor contents in the fermentation of solid substances and the supply of the bioreactor 1 with both atmospheric oxygen or defined gases and medium is achieved pneumatically by compressed air. Via a pressure vessel 44, which in this case is also used as a media storage tank, the air gets into the pressure lid 8 and from there into the vertical or optionally into the horizontal nozzles 16, 28. Between the pressure vessel 44 and the pressure lid 8, there is a stop valve 26. When the stop valve 26 is closed and the stop valve 7 on the bottom of pressure vessel 44 is opened, medium is pressed by the compressed air through the horizontal and optionally also through the vertical nozzle arrangement 10, 20 into bioreactor 1.

Figure 6:
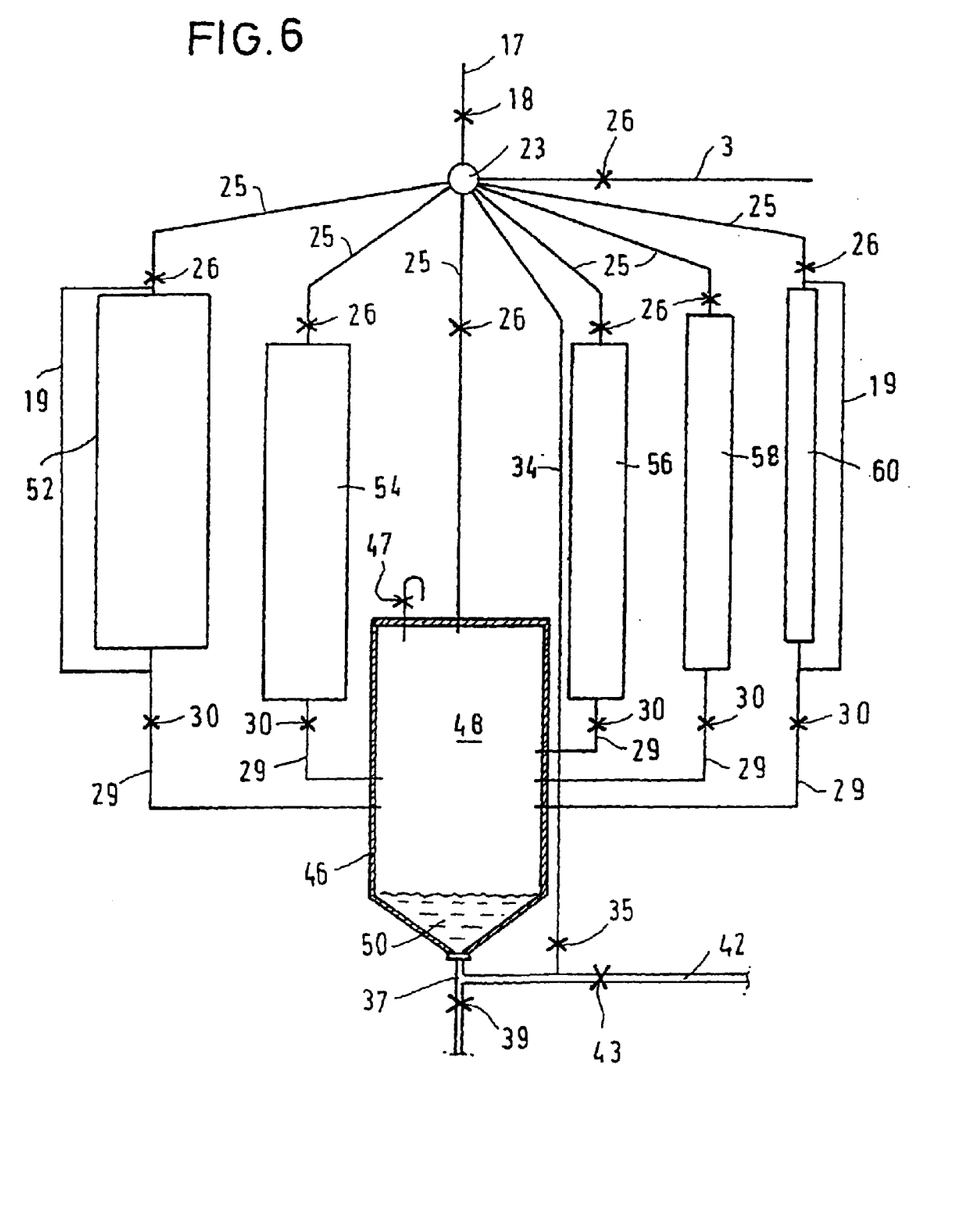
FIG. 6 shows a media mixing and compressed air feeding arrangement for the bioreactor.

FIG. 6 shows an embodiment in which a mixing vessel 46 is connected with the bioreactor 1 instead of pressure vessel 44. Connected to mixing vessel 46 are several pressure vessels 52, 54, 56, 58, 60 which contain different liquid bioreactive substances as well as compressed gas, e.g., compressed air. These different substances can be supplied to the mixing vessel 46, where they can be mixed at a desired ratio. Through the compressed air feed line 17 and the stop valve 18, compressed air gets to a distributing means 23 which distributes the compressed air 48 to all connected pressure vessels 52, 54, 56, 58 and 60, and to the mixing vessel 46. The compressed air feed lines 25 for the individual pressure vessels each have one stop valve 26. The compressed air line 3 for the fermentation vessel 2 also branches off from the distributing means 23.

To be able to selectively introduce different media into the presented bioreactor 1, the pneumatic system is used from several pressure vessels 52, 54, 56, 58, 60 having different volumes. FIG. 6 shows an application with five exchangeable and separately autoclavable pressure vessels (e.g., for medium, two buffers, trace element solution, and antibiotics solution) in which graduated rising pipes 19 indicate the respective filling levels of pressure vessels 52, 54, 56, 58, 60. Through a distributing means 23, the compressed air gets into the pneumatic system. If needed, a part thereof can be directly introduced into the vertical and/or horizontal nozzle arrangement 10, 20 for aerating the bioreactor 1. The independently controllable pressure vessels are connected with the distributing means 23. The respective media from the individual pressure vessels are added to a mixing vessel 46. When the mixing vessel is filled with the different media, a pressure compensation is enabled by a pressure compensating means 47, and compressed air, for example, is pressed into the bottom of the pressure vessel through another compressed gas line 34 of the distributing means 23. This effects the mixing of the different solutions. When the mixing process is completed, the mixing vessel 46 is pressurized with compressed air, and the desired medium is introduced into the horizontal and/or vertical nozzle arrangement 10, 20.

Each pressure vessel may be provided with a rising pipe 19. The feed lines 29 for the bioreactive substances from the pressure vessels each have a stop valve 30.

From the distributing means 23, a compressed gas line 34 further branches off which contains a stop valve 35, wherein the compressed gas line 34 leads to a discharge line 37 at the bottom of the mixing vessel 46 in order to supply compressed air, for example, for the mixing process. The discharge line is provided with a stop valve 39. From the discharge line 37, a feed line 42 with a stop valve 43 branches through which the mixed bioreactive substances 50 can be supplied to the bioreactor 1.

The mixing vessel 46 is further provided with a pressure compensating means 47 for compensating the pressure during the mixing process.

The compressed gas may also be supplied in a pulsing manner to the vertical and/or horizontal nozzle arrangement 10, 20.

Figure 7:
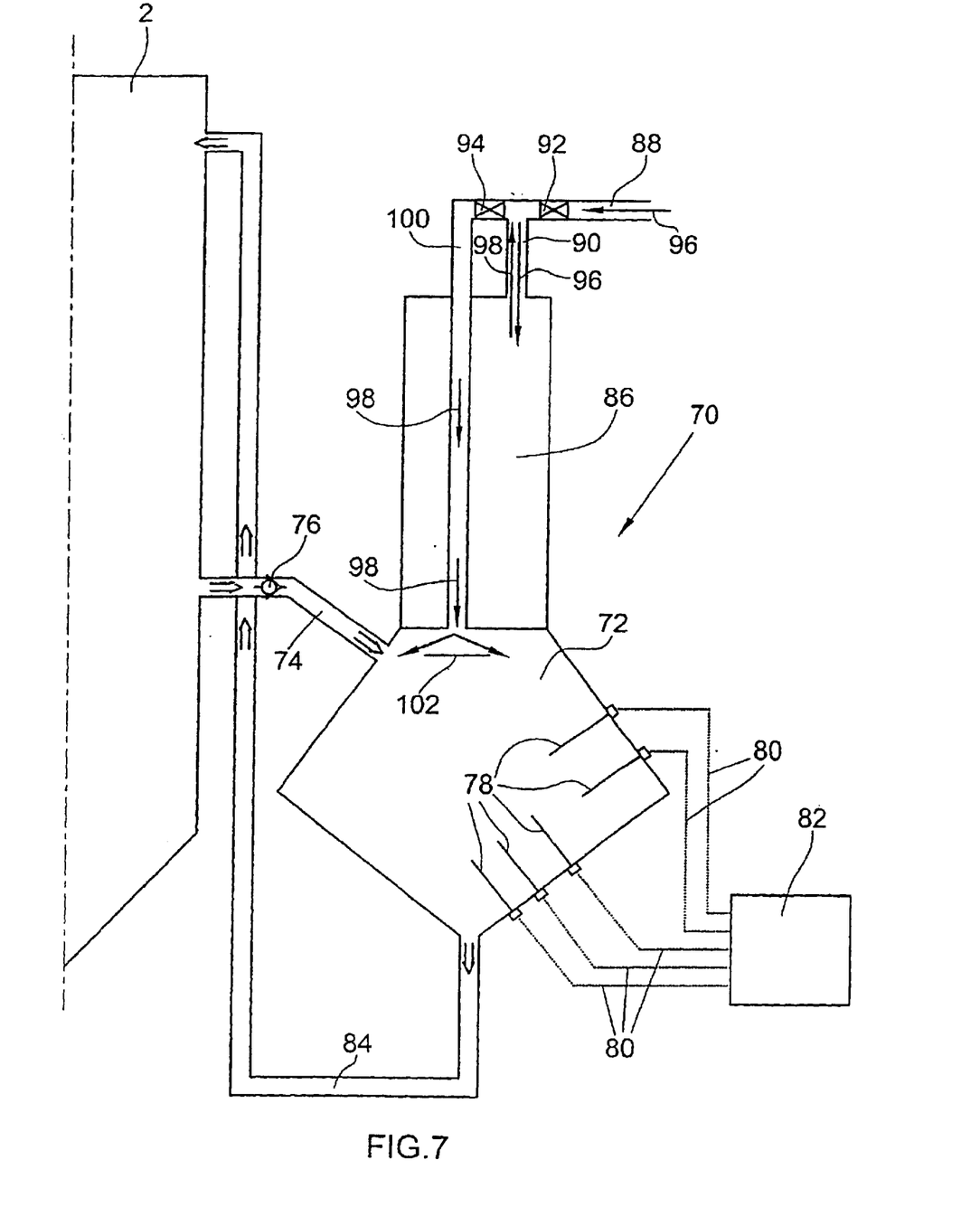
FIG. 7 is a schematic view of a measuring means connected with the fermentation vessel.

A measuring means 70 is connected with the fermentation vessel 2. This measuring means 70 has a measuring chamber 72 which is connected with the fermentation vessel 2 through a feed line 74. Through the feed line 74, the medium to be measured flows from the fermentation vessel 2 into the measuring chamber 72. To set the direction of flow from the fermentation vessel 2 into the measuring chamber 72 independently of the conditions in the measuring chamber 72, a check valve 76 is provided in the feed line 74.

In the measuring chamber 72, several measuring electrodes 78 are provided which are connected through lines 80 with a measuring means 82, which is preferably computer-controlled. The measuring electrodes 78 can effect measurement of, for example, pH, oxygen, temperature and ions.

At the lowest position of the essentially diamond-shaped measuring chamber 72, a recirculating line 84 is connected with the measuring chamber 72. Through the recirculating line 84, the measured medium is recirculated into the fermentation vessel 2.

To recirculate the medium into the fermentation vessel 2, pressure Is applied to the measuring chamber 72. For this purpose, a pressure chamber 86 is assigned to the measuring chamber 72. The pressure chamber 86 is connected with a source of compressed air through lines 88, 90. To produce a positive pressure in the pressure chamber 86, a valve 92 is opened, and a valve 94 is closed, so that the compressed air flows in the direction of arrows 96 into the pressure chamber 86.

To recirculate medium from the measuring chamber 72 through the recirculating line 84 into the fermentation vessel 2, valve 92 is closed, and valve 94 is opened. Thus, compressed air flows from the pressure chamber 86 in the direction of arrows 98 through a line 100 connected with the measuring chamber 72 into measuring chamber 72 and there produces a positive pressure. The defined positive pressure in pressure chamber 86 is directly proportional to the volume of liquid to be displaced in measuring chamber 72. Due to the positive pressure produced in measuring chamber 72, the check valve 76 in the feed line 74 is closed, and the medium present in the measuring chamber 72 is pressed back through recirculating line 84 into the fermentation vessel 2. To achieve a uniform distribution of the air pressure within the measuring chamber and to avoid eddies, a baffle 102 is provided in the region of the inlet of compressed air into measuring chamber 72.

Once the medium has been recirculated from the measuring chamber 72 into the fermentation vessel 2, valve 94 is again closed, and valve 92 is opened. Thereby, a positive pressure again builds within pressure chamber 86. Once the valve 94 is closed, a compensation of pressure occurs in the measuring chamber 72, so that the check valve 76 is again opened by medium flowing from the fermentation vessel 2. The valve 76 may further be a switching valve, for example, in order to control the quantity of medium to be measured which is supplied to the measuring chamber 72.

The present invention also relates to a method for the aerobic fermentation of solid substances, wherein the reaction medium containing said solid substances is mixed by compressed gas 48 supplied to the reaction medium from above. According to the invention, this is effected by introducing the compressed gas directly into the reaction medium using suitable means (such as a vertical nozzle arrangement 10 as described above), so that the spreading gas bubbles effect mixing. Since compressed gas rich in oxygen (such as air, $O_2$-enriched air or $O_2$) is preferably used in aerobic fermentation, the oxygen content in the reaction medium is also increased by this method, which usually accelerates the fermentation additionally. The introducing of the compressed gas may be effected continuously (also referred to as "aeration" in the following) or by pulses of compressed gas (also referred to as "thorough mixing" in the following).

"Solid substrates" within the meaning of the method according to the invention are preferably coal, wood and loaded soils. The method according to the invention is particularly suitable for fermenting coal, especially brown coal. The latter consists of three components defined by their different solubilities as a function of pH:
1. humic acids which can be extracted by 0.1 N NaOH solution;
2. fulvic acids which are also soluble in an acidic medium;
3. the insoluble residue, referred to as the "matrix".

For liquefying the brown coal, the starting product, which may optionally be pretreated or pre-oxidized, in a milled condition (particle size preferably from 0.1 mm to 2 cm, more preferably from 1 to 10 mm), is mixed with an amount of solvent (i.e., water or aqueous-based solvent systems), nutrients, buffers (including buffer substances, acids, bases) and microorganism culture sufficient for solubilization, and cultured with thorough mixing with oxygen-containing compressed gas.

Suitable microorganisms for the solubilization of brown coal include molds, white rot fungi and yeasts. One preferred microorganism for this application is *Trichoderma atroviride*. The nutrients to be employed for this fermentation method highly depend on the species of microorganism employed. In particular, it is preferred to add carbon sources to the microorganism which liquefies the brown coal at the beginning of the reaction to ensure a growth advantage.

Buffer substances which ensure the desired pH value at the respective times of reaction are employed. Thus, at the beginning of the reaction, when a pH of from 5.5 to 6.0 is preferred, and in the liquefying phase, when a pH of from 6.5 to 7.2 is preferred, a citrate/phosphate buffer having a pH of 3 is preferably used, since the fungus itself alkalizes the medium when growing, and only back titration must be performed. It is particularly preferred to set a pH of 5.5 at the beginning of the experiment. The fermentation is preferably performed at a temperature of from 15 to 35° C.

In a preferred embodiment, the brown coal, the brown coal/solvent mixture or the brown coal/solvent/nutrient mixture is sterilized or tyndallized prior to the addition of the fermenting microorganisms. This is preferably performed by several cycles of heating at temperatures of above 75° C., preferably above 80° C., for at least 45 minutes, followed by cooling down to room temperature for several hours.

In the 80° C. steps, the physiologically active microorganisms in the substrate, medium and reactor space, but not dormant spores, are killed. In the periods of time with moderate temperatures, the spores germinate, and are killed in the subsequent heating step.

Conventional tyndallization means three cycles of heating of a liquid or nutrient medium. In the intervals between the temperature steps, the product is kept at room temperature (Eckhard Bast, 1999, Mikrobiologische Methoden: eine Einführung in grundlegende Arbeitstechniken—Heidelberg, Berlin; Spektrum Akademischer Verlag, ISBN 3-8274-0786-9).

The microbially solubilized coal obtainable according to the present invention can be used as a carbon and energy source for bacteria which are capable of producing a chemically characterized substance, such as polyhydroxyfatty acids for the synthesis of biodegradable plastics, from the chemically heterogeneous mass product coal (A. Steinbüchel and B. Füchtenbusch, Proceedings ICCS 97, 1673–1676 (1997)). The aliphatic residue which cannot be liquefied microbially and has a lower proportion of water and ashes and thus a higher gross calorific value can be used, on the one hand, for direct thermal utilization (R. Köpsel et al., Freiberger Forschungshefte, 159–166 (1998)), and on the other hand, for further subsequent fermentation processes by aliphatic-degrading yeasts (U. Hölker et al., Proceedings of the 16th SMYTE, Slovakia, page 16 (1998); Folia Microbiol. 44, 226–227 (1999)).

It is particularly preferred to perform the method according to the invention in the above described bioreactor.

The present invention is further illustrated by the following Example.

EXAMPLES

General procedures

The product "liquefied coal" was defined as the sample supernatant obtained after 20 min of centrifuging at 10,000× g. The degree of liquefaction was determined from the optical density at 450 nm or from the dry weight of the supernatant. To separate the humic acid compounds from fulvic acid compounds, the supernatant was acidified to pH 1.5 and again centrifuged. The liquefied products were characterized with respect to their optical densities, humic and fulvic acid contents and bacterial contamination by means of incubation of samples in complete media followed by microscopic analyses.

Example 1

Fermentation of Brown Coal

A bioreactor according to the invention (as shown in FIGS. 1 to 6 having a vertical nozzle arrangement (10), a pressure lid (8) with pipes (14) having nozzles (16) and extending to the bottom of the reactor space (49), and a rigid horizontal nozzle arrangement (20); volume; 25 l) was charged with 2,500 g of brown coal (Bergheim Lithotyp A, particle size from 2 to 10 mm, water content of the coal about 50%) as a solid to be converted in 10 l of water. As the coal-solubilizing aerobic fungus, *Trichoderma atroviride* was employed (U. Hölker et al., Fuel Processing Technol., 52, 65–71 (1997)). Fifty grams of glutamate was added to initiate the induction of coal-liquefying enzymes (U. Hölker et al., Appl. Microbiol. Biotechnol. 44, 351–255 (1995)). The initial pH was 5.8 in order to provide the fungus with a growth advantage at first over the bacteria present in the coal. The continuous air pressure sufficient for aeration was 0.4 bar. The air pressure was increased to 3 bar for 10 s daily by the vertical nozzle arrangement 10 in order to thoroughly mix the reactor contents.

Figure 8:
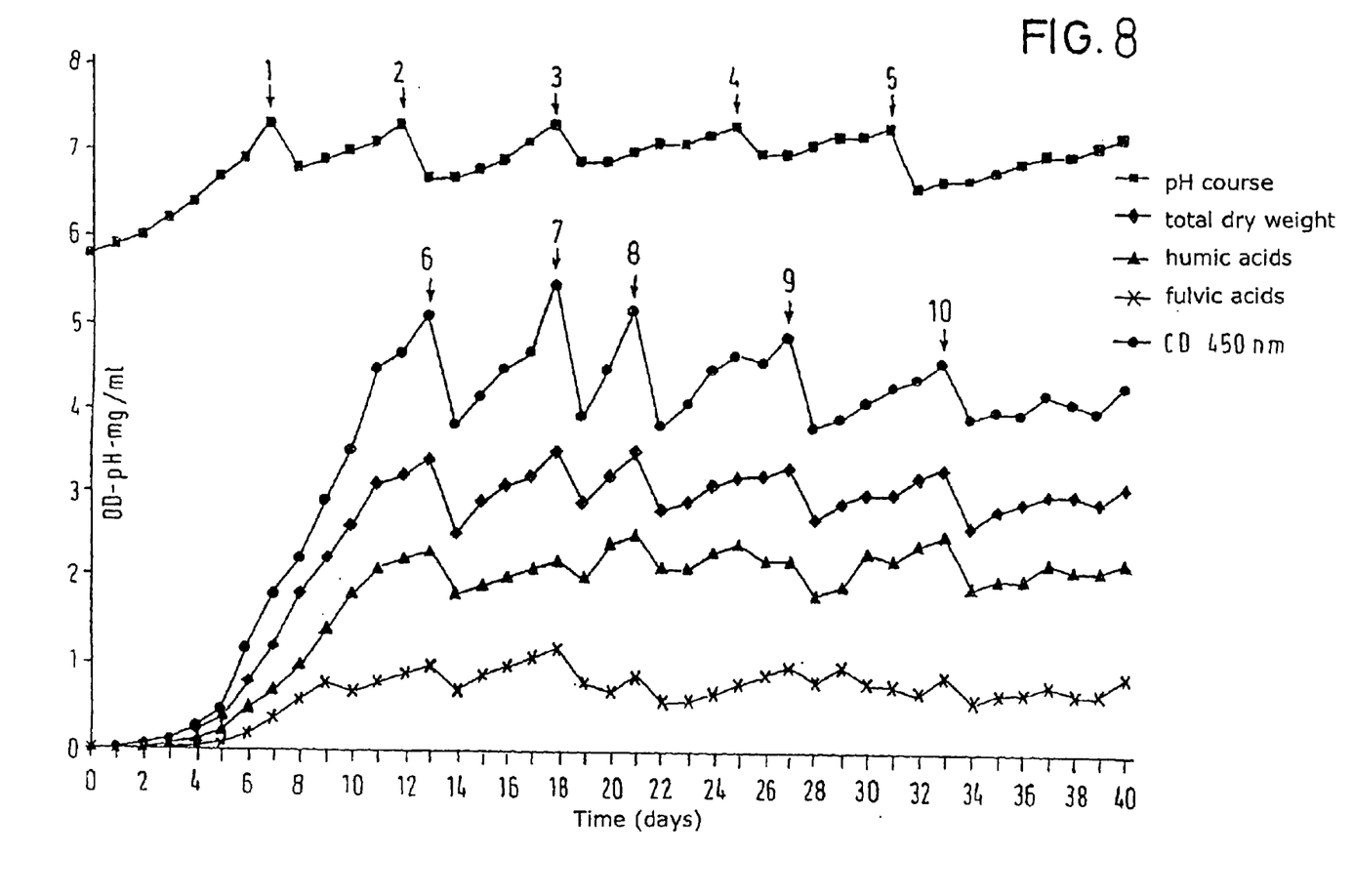
FIG. 8 shows the course of reaction of the fermentation charge described in Example 1.

In a semicontinuous approach, 800 ml of water was added through the horizontal nozzle arrangement (20) at intervals of 24 hours, and the same quantity of reactor contents was withdrawn at the discharge system. In this suspension, the optical density, pH, humic and fulvic acid contents were determined and checked for bacterial contamination. If the pH value reached 7.3, it was titrated back to 7.0 via the media supply system (FIG. 8, arrows 1–5).

The recovery of solubilized coal sought in this fermentation approach was 3 mg of dry weight per ml of suspension at pH 7 per day and should be kept constant continuously over a period of 30 days. This corresponds to a sought recovery of about 2 g of solubilization products per day. When the recovery increased beyond 3.3 mg of dry mass per ml, the reactor contents were diluted by adding water through the media supply system and again adjusted to the desired concentration (FIG. 8, arrows 6–10).

After a fermentation period of 12 days, the sought concentration of solubilized coal was reached, and within a period of another 28 days, 71 g of solubilization products was produced in the proposed bioreactor.

Example 2

Method for the Mild Sterilization of Bioreactors with Contents; Modified Tyndallization A bioreactor according to the invention (as shown in FIGS. 1 to 6, having an insertable vertical nozzle arrangement (10) with short pipes (14), devices for heat exchange (51a, 51b, 51c) in the outer wall of a rotating horizontal nozzle arrangement (20) and a measuring means (70); volume: 12.5 l–) was charged exactly as described in Example 1. The pressure lid (8) was closed and the nozzles (16) were thus pneumatically pressed into the substrate. The pneumatic recirculating and measuring system was activated, and at one-minute intervals, the medium was pumped past the temperature sensor of the measuring chamber and through the horizontal nozzle system (20) back into the bioreactor. Water was heated in a thermostat at 95° C. and pumped through the jacket of the bioreactor (51a, 51b, 51c) until the temperature in the interior reached 80° C. This temperature was maintained for 45 min (with constant aeration/thorough mixing by the vertical nozzle system (10) and recirculating of the medium through the horizontal nozzle system (20)). Subsequently, the bioreactor was cooled down to 25° C. by temperature-controlled water in the jacket, while it was aerated, thoroughly mixed and recirculated for 12 hours. Subsequently, the temperature in the bioreactor space was again adjusted to 80° C. for 45 minutes as before. This was again followed by cooling down to 25° C. for 20 hours, and then a third heating of the reactor interior to 80° C. for 45 min.

To verify that a successful sterilization had taken place, the bioreactor was subsequently further thoroughly mixed, aerated and recirculated. Daily (for 7 days), 1 ml samples were taken and used to inoculate both Petri dishes (1.2% agar) and 50 ml liquid cultures containing the nutrient medium used in the bioreactor. The Petri dishes were incubated at 25° C. for 72 hours, and the liquid cultures were incubated at 255° C. and 120 rpm on a vibrator. It was found that no contaminations could be detected under such conditions in the reactor space.

After the sterility control had been performed, the bioreactor was inoculated with the coal-solubilizing fungus *T. atroviride*, and the coal was fermented by analogy with Example 1, but at a set temperature of 25° C. to obtain 60 g of liquefied product.

What is claimed is:

1. A bioreactor for fermenting solid substrates, comprising a fermentation vessel, a charging means for bioreactive substances, and at least one nozzle arrangement within said fermentation vessel for aeration and thorough mixing of the substrates, wherein the at least one nozzle arrangement has a multitude of pipes extending in parallel into a reaction space of the fermentation vessel and provided with nozzles, wherein a first, vertically extending nozzle arrangement can be extended into and retracted from the reaction space of the fermentation vessel, and having a second, horizontal nozzle arrangement with at least one pipe having nozzle orifices and extending horizontally through the reaction space.

2. The bioreactor according to claim 1, wherein a second, horizontal nozzle arrangement is provided which consists of at least two interconnected pipes extending horizontally and in parallel through the reaction space, each having a plurality of nozzle orifices.

3. The bioreactor according to claim 1, wherein said horizontal nozzle arrangement can be rotated around a horizontal rotation axis.

4. The bioreactor according to claim 1, wherein said fermentation vessel has a bottom section with a tapering cross-section.

5. The bioreactor according to claim 4, wherein said bottom section is conically designed and leads into a draining channel which is inclined from horizontal and has a draining valve at the lowest position thereof.

6. The bioreactor according to claim 1, wherein said at least one nozzle arrangement receives compressed gas from a pressure vessel.

7. The bioreactor according to claim 6, wherein said pressure vessel contains a bioreactive liquid substances, wherein said bioreactive liquid substance is brown coal suspended in a liquid and the liquid has a pH in range of 5–7 pH unit in addition to said compressed gas.

8. The bioreactor according to claim 7, wherein said at least one nozzle arrangement alternatively receives compressed air or said liquid bioreactive substance from said pressure vessel.

9. The bioreactor according to claim 1, wherein said at least one nozzle arrangement can be pressurized with pulsing compressed air.

10. The bioreactor according to claim 1, wherein said second nozzle arrangement is provided within said fermentation vessel in a height-adjustable manner.

11. The bioreactor according to claim 7, wherein a multitude of pressure vessels pressurized with compressed air and connected to a mixing vessel are provided which contain different liquid bioreactive substances.

12. The bioreactor according to claim 11, wherein said mixing vessel has a pressure compensating means.

13. The bioreactor according to claim 11, wherein said pressure vessels are exchangeable and can be separately autoclaved.

14. The bioreactor according to claim 5, wherein said draining channel is covered by a wire mesh.

15. The bioreactor according to claim 1, wherein a pressure lid of said fermentation vessel accommodates said first nozzle arrangement whose pipes extend vertically from the pressure lid into the reaction space.

16. The bioreactor according to claim 15, wherein said vertical pipes of said first nozzle arrangement are provided in said pressure lid to be exchangeable.

17. The bioreactor according to claim 1, wherein said fermentation vessel is connected through a feed line with a measuring chamber, which is again connected through a recirculating line with said fermentation vessel, and said measuring chamber can be pressurized for recirculating measured media.

18. The bioreactor according to claim 1, wherein a device for heat exchange is provided comprising a device:
(i) in which said fermentation vessel has a double wall and the thus formed cavity can be flowed through with temperature-controlled heat exchange fluids through a connecting pipe and discharge pipe; and/or (ii) which is a horizontal pipe system within said fermentation vessel which can be flowed trough with a temperature-controlled heat exchange fluid.

19. A method of producing a fermentation product, said method comprising the aerobic fermentation of a reaction medium comprising solid substrates, wherein said reaction medium comprises brown coal, culture medium, and a microorganism capable to ferment said solid substrate to produce a fermentation product, and the recovery of the fermentation product produced, wherein said reaction medium containing the solid substrates is thoroughly mixed by compressed gas supplied to said reaction medium from above.

20. The method according to claim 19, wherein said thorough mixing is effected by a continuous stream of compressed gas or by compressed gas pulses.

21. The method according to claim 19, wherein said solid substrates are selected from the group consisting of coal, wood and loaded soils.

22. The method according to claim 21, wherein said solid sub is coal.

23. The method according to claim 22, wherein the solid substrate is brown coal also known as lignite.

24. The method according to claim 22, which further comprises adding a microorganism capable to ferment said solid substrate, nutrients and/or buffers to said reaction medium.

25. The method according to claim 23, wherein, said brown coal or the reaction medium containing said brown coal is tyndallized together with a bioreactor prior to fermentation or prior to the addition of a microorganism.

26. The method according to claim 23, wherein:
(i) said brown coal has a particle size of from 1 to 10 mm;
(ii) a microorganism is added to the reaction medium, and the microorganism is selected from the group consisting of molds, yeasts and white rot fungi;
(iii) the pH of the reaction medium is from 5.5 to 6.0 at a beginning of the reaction;
(iv) the pH is maintained at from 6.5 to 7.2 during a solubilization phase;
(v) the fermentation is performed at a temperature of from 25° C. to 30° C.; and/or (vi) from 1 to 25 liter of compressed air per liter of fermentation broth per day is passed through the reaction medium.

27. The method according to claim 26, wherein the microorganism added to said reaction medium is Trichoderma atroviride.

28. The method according to claim 19, wherein said fermentation is performed in a bioreactor comprising a fermentation vessel, a charging means for said reaction medium, and at least one nozzle arrangement within said fermentation vessel for aeration and thorough mixing of the substrates, wherein the at least one nozzle arrangement has a multitude of pipes extending in parallel into a reaction space of the fermentation vessel and provided with nozzles, wherein a first, vertically extending nozzle arrangement can be extended into and retracted from the reaction space of the fermentation vessel, and having a second, horizontal nozzle arrangement with at least one pipe having nozzle orifices and extending horizontally through the reaction space.

* * * * *

UNITED STATES PATENT AND TRADEMARK OFFICE
CERTIFICATE OF CORRECTION

PATENT NO.    : 6,797,508 B1
DATED         : September 28, 2004
INVENTOR(S)   : Holker It is certified that error appears in the above-identified patent and that said Letters Patent is hereby corrected as shown below:

Column 1,
Line 12, "it Is required" should read -- it is required --.
Line 59, "used In any" should read -- used in any --.

Column 3,
Line 29, "shown In" should read -- shown in --.

Column 6,
Line 16, "can be Introduced" should read -- can be introduced --.

Column 7,
Line 52, "pressure Is applied" should read -- pressure is applied --.

Column 10,
Line 49, "volume: 12.5 1-)" should read -- volume: 12.5 1) --.

Column 11,
Line 50, "liquid substances" should read -- liquid substance --.

Column 12,
Line 27, "flowed trough" should read -- flowed through --.
Lines 44-45, "solid sub" should read -- solid substrate --.

Signed and Sealed this

Twenty-third Day of August, 2005

JON W. DUDAS
*Director of the United States Patent and Trademark Office*